(12) United States Patent
Brereton

(10) Patent No.: US 10,189,719 B1
(45) Date of Patent: Jan. 29, 2019

(54) PROCESS FOR THE MANUFACTURE OF LITHIUM METAL OXIDE CATHODE MATERIALS

(71) Applicant: Nano One Materials Corp., Burnaby (CA)

(72) Inventor: Clive H. M. Brereton, Vancouver (CA)

(73) Assignee: Nano One Materials Corp., Burnaby (CA)

(*) Notice: Subject to any disclaimer, the term of this patent is extended or adjusted under 35 U.S.C. 154(b) by 6 days.

(21) Appl. No.: 15/662,380

(22) Filed: Jul. 28, 2017

(51) Int. Cl.
| | |
|---|---|
| H01B 1/08 | (2006.01) |
| C01G 51/00 | (2006.01) |
| C01G 45/00 | (2006.01) |
| C01B 13/36 | (2006.01) |
| C01B 25/45 | (2006.01) |
| C01G 45/02 | (2006.01) |
| C01G 53/00 | (2006.01) |

(52) U.S. Cl.
CPC ............ *C01G 45/006* (2013.01); *C01B 13/36* (2013.01); *C01B 25/45* (2013.01); *C01G 45/02* (2013.01); *C01G 51/006* (2013.01); *C01G 51/44* (2013.01); *C01G 53/50* (2013.01); *H01B 1/08* (2013.01); *C01P 2006/40* (2013.01)

(58) Field of Classification Search
CPC ......... H01B 1/00; H01B 1/08; H01M 4/0471; H01M 4/1391; C01G 51/04; C01G 53/04
See application file for complete search history.

(56) References Cited

U.S. PATENT DOCUMENTS

| | | | | |
|---|---|---|---|---|
| 5,281,494 A | * | 1/1994 | Ettel | C01G 53/04 |
| | | | | 252/182.1 |
| 6,383,235 B1 | * | 5/2002 | Maegawa | C01G 45/1242 |
| | | | | 29/623.5 |
| 9,296,623 B2 | * | 3/2016 | Naoi | B82Y 30/00 |

(Continued)

FOREIGN PATENT DOCUMENTS

CA 2905519 * 9/2014

OTHER PUBLICATIONS

Fu et al "Electrode materials for lithium seconday batteries prepared by sol-gel methods", Progress in Materials Science 50 (2005) 881-928. (Year: 2005).*

*Primary Examiner* — Marc Kopec
(74) *Attorney, Agent, or Firm* — Joseph T. Guy; Patent Filing Specialist, Inc.

(57) ABSTRACT

An improved process is provided for forming a precursor to a lithium metal oxide. An improved lithium metal oxide formed by calcining the precursor is also provided. The process includes providing lithium bicarbonate in a first aqueous mixture. The lithium bicarbonate is then reacted with metal acetate thereby forming a second aqueous mixture comprising metal carbonate, lithium acetate, acetic acid and water wherein the acetic acid is neutralized with lithium hydroxide thereby forming a first mixture comprising metal carbonate and lithium acetate. The first mixture is separated into a second mixture and a third mixture wherein the second mixture comprises the metal carbonate and a first portion of lithium acetate with metal carbonate and lithium acetate being in a predetermined molar ratio. The third mixture comprises a second portion of lithium acetate. The second mixture is dried thereby forming the precursor comprising metal carbonate and lithium acetate in the predetermined molar ratio.

55 Claims, 2 Drawing Sheets

(56) References Cited

U.S. PATENT DOCUMENTS

| | | | |
|---|---|---|---|
| 9,698,419 B1 | 7/2017 | Frianeza-Kullberg et al. | |
| 2004/0229124 A1* | 11/2004 | Miyamoto | H01M 10/0525 |
| | | | 429/231.1 |
| 2005/0153206 A1* | 7/2005 | Oesten | H01M 4/366 |
| | | | 429/232 |

* cited by examiner

PROCESS FOR THE MANUFACTURE OF LITHIUM METAL OXIDE CATHODE MATERIALS

BACKGROUND

The present invention is related to an improved process for the manufacture of NMC cathode materials. More specifically, the present invention is related to an improved process for the formation of precursors of lithium metal oxide comprising at least one of nickel, manganese and cobalt salts. Even more specifically, the present invention is related to a process for making precursors of lithium metal oxide requiring low water consumption and recycle of key reactants.

One of the more promising cathode materials for batteries is an oxide comprising various ratios of nickel, manganese and cobalt, such as those referred to in the art as NMC's, wherein an NMC is general represented by the chemical formula:

$$Li_{2-x-y-z}Ni_xMn_yCo_zO_2$$

wherein x+y+z≤1; and wherein the formula is represented in stoichiometric balance with the understanding that the lithium is mobile and functions as the charge carrier into and out of the cathode as is known in the art.

The process of forming lithium metal oxides includes the formation of a powder comprising salts of the metals followed by calcining of the powder to achieve the oxide in a crystallographic ordered lattice. The unit cells of the crystallographic ordered lattice comprise layers and the lithium can migrate into and out of the layers. There are two primary ways of forming the powder, or precursor. The traditional approach is to intimately mix salts of the metals to form a homogeneous mixture. The homogenous mixture can be formed by many techniques including physical mixing of the solids, co-precipitation, sol-gel and the like, each of which is characterized by the formation of a mixture of metal salts with the choice of technique partially determined by the desired particle size and degree of homogeneity both of which are thought to impact the properties of the ultimate oxide even though quantification of the benefits is difficult to ascertain. Techniques which rely on the mixing of metal salts to form a powder, and preferably a homogenous powder, are characterized by the formation of an amorphous mixture of separate salts.

A modern technique has recently come to the fore as a significant improvement over the mere mixing of salts. The modern technique, referred to in the art as complexometric or complexecelle formation, forms ordered crystalline precursors of metal salts instead of an intimate mixture of powders. The complexometric method relies on carefully controlled precipitation conditions to precipitate an ordered precursor comprising salts of the metals ultimately incorporated in the lithium metal oxide. By way of a non-limiting example, a precursor for forming a lithium metal oxide with equal proportions of nickel, manganese and cobalt would be in the form of an ordered lattice comprising an equal molar concentration of a nickel salt, a manganese salt and a cobalt salt. While not limited to theory, it is hypothesized that by having an ordered lattice of metal salts, as opposed to a mixture of powdered metal salts, the metal migration during the calcining is more efficient thereby allowing the ordered lattice of oxides to have fewer dislocations, fewer crystalline impurities or fewer inactive phases even though this has proven difficult to quantify. Oxides formed from the precursor prepared by the complexometric method have proven to be advantageous with regards to their properties as a cathode in a battery.

The complexometric method, which relies on balancing the solubility of metal salts to precipitate the metal salts in an ordered lattice, requires copious amounts of water and therefore the cost of the process, though advantageous over solid state methods, limits the manufacturing scale achievable within a reasonable space and with reasonable resources as the water must be removed prior to calcining. Removing large volumes of water is neither cost effective nor conducive to a large scale process. Furthermore, the process utilizes materials, such as ammonia or ammonium hydroxide, for pH control which increases the complexity in a manufacturing environment as the ammonia must be removed and either disposed of or recycled neither of which is conducive to environmental stewardship or effective manufacturing practice.

The conventional complexecelle method, as applied to the formation of a precursor for a lithium nickel manganese nickel oxide (NMC), will be described with reference to the flow chart of FIG. 1. In FIG. 1, water and lithium carbonate (A) are introduced to a mixer ($M_a$). Carbon dioxide (B) is introduced to mixer ($M_a$) thereby forming an aqueous solution of lithium bicarbonate (C) in accordance with reaction Scheme 1:

$$Li_2CO_3 + CO_2 + H_2O \rightarrow 2LiHCO_3 \quad \text{Scheme 1.}$$

The lithium bicarbonate is introduced to reactor ($R_a$) and metal acetate (D) is metered in thereby forming metal carbonate and lithium acetate. Ammonia (E) is introduced to maintain pH leading to the mixture (F) in accordance with reaction Scheme 2:

$$LiHCO_3 + MAc_2 + NH_3 MCO_3 + LiAc + NH_4Ac \quad \text{Scheme 2}$$

wherein Ac represents acetate.

Mixture (F) is then separated in separator ($S_a$), into a liquid stream (G) comprising a large volume of water, possibly metals complexed by ammonia, residual acetates, etc. thereby representing a waste stream of high volume, per mole of solids obtained. The solid component (H), from the separator ($S_a$), comprises primarily the precursor comprising metal carbonates in an ordered lattice and lithium acetate.

The present invention provides a method of complexometric formation wherein the volume of water required, as a function of the oxide precursors formed, is minimized due to recycling and the inventive method allows for a near continuous flow operation wherein most components not incorporated in the final product are maintained within a steady state manufacturing loop for subsequent reuse.

SUMMARY OF THE INVENTION

It is an object of the invention to provide an improved process for the manufacture of lithium meal oxide cathode materials and, more specifically, the precursors to the oxide suitable for use in lithium metal oxide cathode materials.

A particular feature of the invention is the ability to prepare precursors for lithium metal oxide cathode materials in a process using much less water and wherein a portion of the water can be recycled.

Yet another particular feature is the ability to recycle those elements used primarily for pH control.

These and other embodiments, as will be realized, are provided in a process for forming a precursor to a lithium metal oxide. The process includes providing lithium bicarbonate in a first aqueous mixture. The lithium bicarbonate is then reacted with metal acetate thereby forming a second aqueous mixture comprising metal carbonate, lithium acetate, acetic acid and water wherein the acetic acid is neutralized with lithium hydroxide thereby forming a first mixture comprising metal carbonate and lithium acetate. The first mixture is separated into a second mixture and a third mixture wherein the second mixture comprises the metal carbonate and a first portion of lithium acetate with metal carbonate and lithium acetate being in a predetermined molar ratio. The third mixture comprises a second portion of lithium acetate. The second mixture is dried thereby forming the precursor comprising metal carbonate and lithium acetate in the predetermined molar ratio.

DESCRIPTION

The present invention is related to an improved process for forming lithium metal oxide cathode materials and, particularly, improvements in the precursors used to prepare lithium metal oxides.

Figure 1:
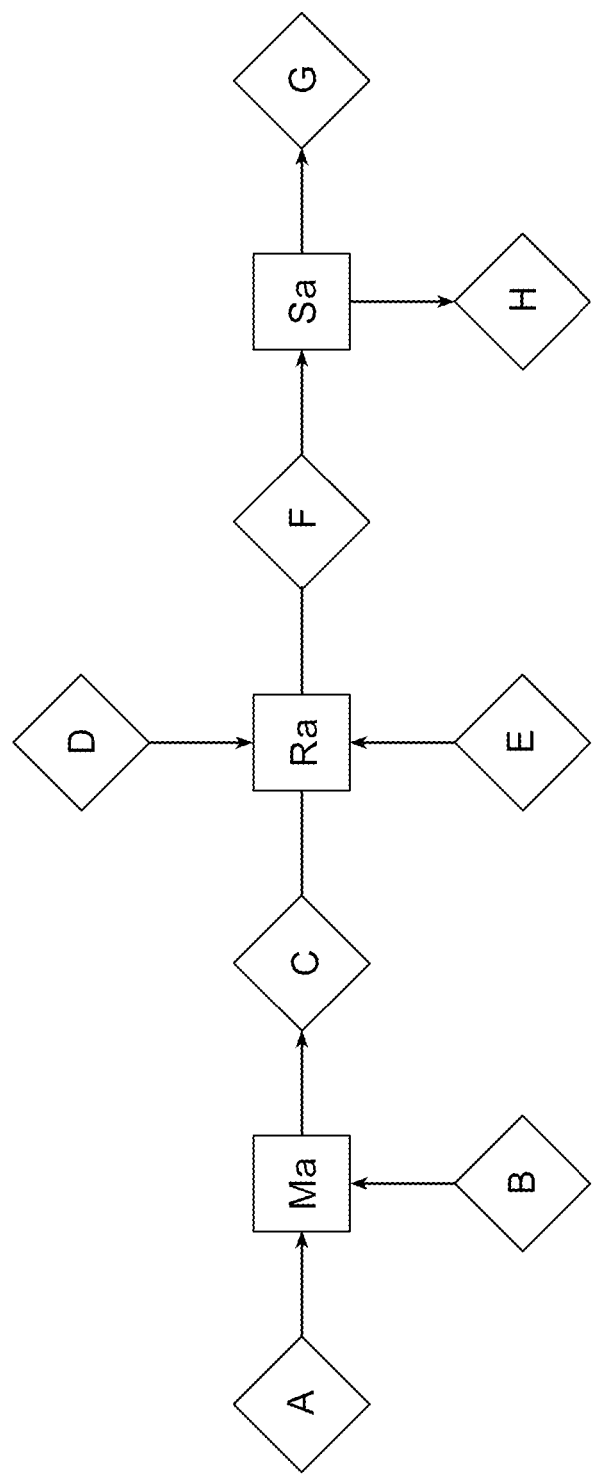
FIG. 1 is a flow chart representation of the prior art.
Figure 2:
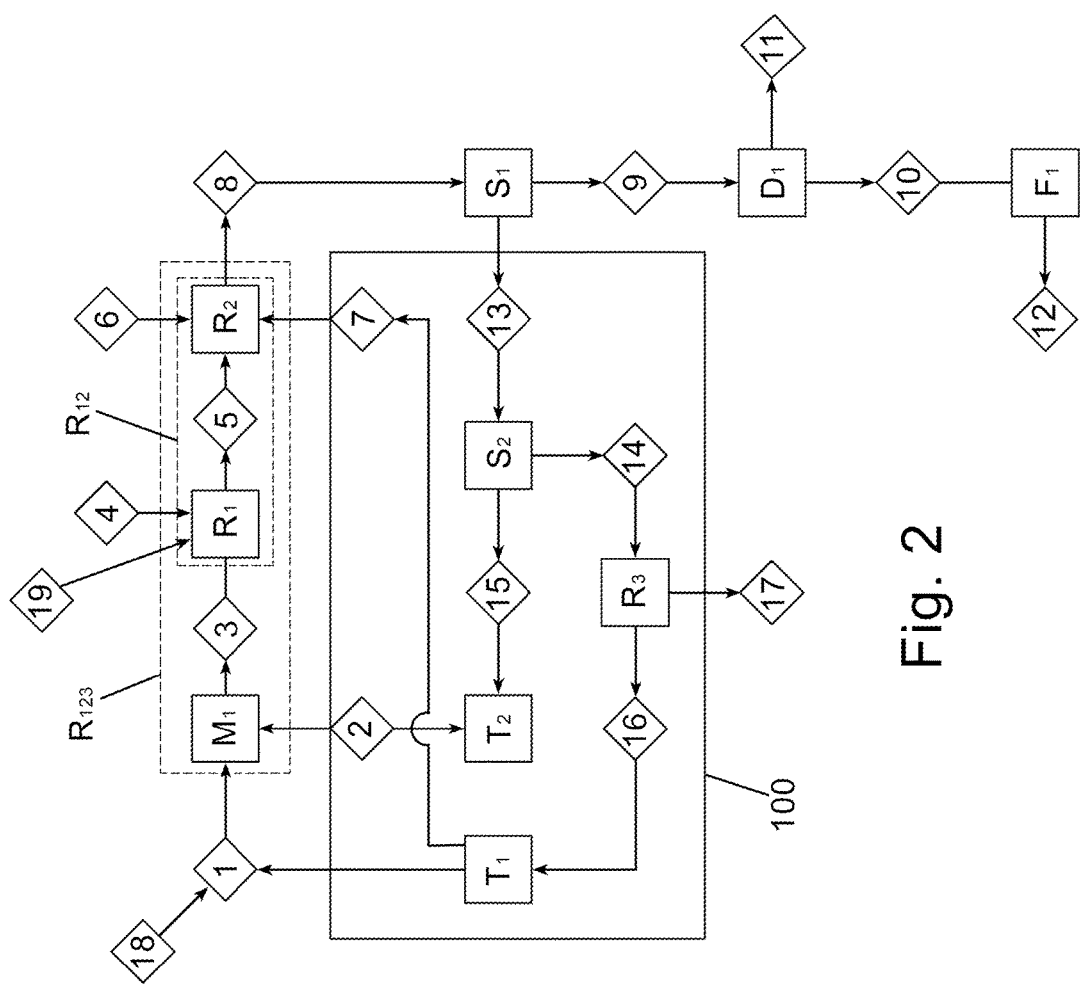
FIG. 2 is a flow chart representation of an embodiment of the invention.

An embodiment of the invention will be described with reference to the flow chart of FIG. 2. In FIG. 2, an aqueous lithium hydroxide (1), is optionally introduced to a mixer ($M_1$). Lithium hydroxide can be from the recycle loop, as will be discussed, or the lithium hydroxide can originate from virgin lithium hydroxide (18), which is preferably added as a solid, and allowed to dissolve, or some combination thereof during steady state manufacturing. A solution containing lithium acetate (2), which may be primarily recycled lithium acetate, is optionally mixed with the lithium hydroxide in mixer ($M_1$) thereby forming a mixture (3) of lithium hydroxide and lithium acetate. The lithium acetate is preferably an aqueous solution and the product of a recycle loop as will be described further herein. One of the advantages of the process lies in the fact that, by recycle of a solution which is predominantly lithium acetate, while removing the metal carbonate and an appropriate amount of lithium acetate, it is possible to take advantage of the high solubility of the lithium salts, hydroxide, acetate and bicarbonate, and the low solubility of the transition metal carbonates. Removing the transition metal carbonates, and resaturation of the solution with lithium bicarbonate by further addition of carbon dioxide, allows for the reuse of the bulk of the solution thereby mitigating the necessity for the addition of copious amounts of water as usually required due to the limited solubility of lithium bicarbonate. Lithium hydroxide is preferably in a concentration of up to about 5 molal or 5 moles of lithium hydroxide per kg of water without limit thereto. Lower concentrations of lithium hydroxide can be used, however, the larger the amount of water introduced with the lithium hydroxide the greater the amount of evaporation required in the eventual downstream drier, D1, which is undesirable. As will be realized, lithium is consumed in the reaction and therefore makeup lithium is necessarily added to the process in an amount which is approximately the stoichiometric equivalent to the product formed. Lithium can be added as lithium hydroxide (18) and be incorporated as a component of the lithium hydroxide feed or alternatively lithium carbonate (19) can be added preferably as a solid and allowed to dissolve as lithium bicarbonate by reaction with carbon dioxide.

Mixture (3), and lithium carbonate (19) if utilized, is reacted with carbon dioxide (4) in reactor ($R_1$), which may be the same as mixer ($M_1$), thereby forming lithium bicarbonate as mixture (5) wherein mixture (5) comprises lithium bicarbonate and optionally lithium acetate preferably from the recycle loop. Metal acetate (6), preferably in water, is metered into mixture (5) in reactor ($R_2$). A sufficient amount of metal acetate is preferably added to achieve a molar amount of metal equivalent to the moles of carbonate/bicarbonate in mixture (5). While theoretically, the metal acetate and carbonate can be in stoichiometric balance this is difficult to achieve in a manufacturing scale and therefore the practical condition is a slight excess of carbonate to insure all metal is precipitated. Metal acetate is preferably a mixture of metal acetates wherein the metals are in the stoichiometric ratio of the intended oxide and is preferably a mixture comprising nickel acetate, manganese acetate and cobalt acetate in accordance with their intended molar ratio in the intended lithium metal oxide. As would be realized, mixer ($M_1$), and the reactors $R_1$ and $R_2$ are illustrated as separate components for the purposes of illustration and they may be distinct elements, however, $R_1$ and $R_2$ can be a common vessel, represented as $R_{12}$, or $M_1$, $R_1$ and $R_2$ may all be a common vessel, represented as $R_{123}$. While metal acetates are preferred other organic acids, particularly carboxylic acids, can be employed wherein the base, or deprotanated salt of the acid, complexes the metal. In one embodiment the organic acid comprises at least one carboxylic acid group. In some embodiments multiple carboxylic acid groups can be employed in the organic acid moiety with an appropriate adjustment to the stoichiometry. Particularly preferred multiple carboxylic acid groups are small to facilitate ligation with oxalic acid being a particularly preferred di-carboxylic acid. It is preferable that metal salt comprise a salt of an organic acid with no more than three carboxylic acid groups, more preferably no more than two and preferably one. It is preferred that the metal comprise a salt of an organic acid comprising no more than 10 alkly carbons, preferably no more than 5, more preferably no more than 2 and most preferably 1.

A particular advantage of the invention is the pH adjustment with lithium hydroxide (7). It is preferable to maintain a pH in the reactor ($R_2$) of about 7-9 to insure precipitation of the metal carbonates. Through ligand exchange the carbonates, of lithium bicarbonate, form insoluble metal carbonates and, stoichiometrically, lithium acetate thereby forming mixture (8) comprising the desired metal carbonates, as the precursor to the oxide, and lithium acetate as well as any excess lithium, excess acetate and water. A particular feature of mixture (8) is the absence of ammonia as required in the conventional complexecelle method. The stoichiometric reaction at reactor ($R_2$) is represented by reaction Scheme 3:

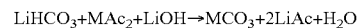
$LiHCO_3 + MAc_2 + LiOH \rightarrow MCO_3 + 2LiAc + H_2O$   Scheme 3

A particular advantage of the instant invention is the fact that the addition of lithium hydroxide to achieve pH balance is a stoichiometric reaction with the formation of metal carbonate wherein two moles of lithium acetate are generated per mole of metal carbonate thereby providing a one mole excess of lithium acetate. A particular feature of the invention is the ability to recycle the excess mole of lithium as will be further described herein. Such recycle allows the lithium to be used as the neutralizing chemical in the complexelle process which is highly advantageous due to the high cost of this material.

Returning to FIG. 2, mixture (8) is split at splitter ($S_1$) into two portions. One portion is a solids containing component (9), comprising the metal carbonate as an ordered lattice, lithium acetate and water. In the solids containing component (9) the lithium acetate and metal carbonate are in a predetermined molar ratio and preferably a 1:1 molar ratio as will be described further herein. The solid containing component (9) is dried in drier ($D_1$) to remove water (11) thereby providing a dry precursor to the oxide (10), comprising primarily metal carbonate and lithium acetate. The dry precursor is calcined in a furnace ($F_1$) to yield the lithium metal oxide (12). The removed water (11) may be waste or it may be recycled as solvating water for the lithium hydroxide or metal acetate.

The liquid component (13) primarily comprises water and lithium acetate and represents a particular feature of the instant invention which is an optional but preferred lithium recycle loop, 100.

A portion of the liquid component (13) is split at splitter ($S_2$) thereby providing a first lithium acetate (15) stream ultimately providing an optional supply of lithium acetate (2) for conversion to lithium bicarbonate. An optional storage tank ($T_2$) can be used to provide storage for the lithium acetate from which the mixer ($M^1$) is supplied or for storage and receipt of virgin lithium acetate. The second lithium acetate stream (14) is preferably split into lithium hydroxide solution (16) and acetic acid solution (17) by a salt splitter ($R_3$). The lithium hydroxide solution (16) can be used as a supplement to lithium hydroxide solution (1) or for pH adjustment (7). Independent of where it is added, the amount of this lithium hydroxide must necessarily equal the amount of lithium hydroxide required to neutralize an excess amount of acetic acid produced in a reactor R2, described below, which is also equal to the amount of acidity introduced with the carbon dioxide stream 4 described below. An optional storage tank ($T_1$) can be used to provide storage for the lithium hydroxide from which the mixer ($M^1$) is supplied or for storage and receipt of solid lithium hydroxide dissolved for subsequent use. At steady state, the moles of lithium introduced into the process are equivalent to the moles of lithium in the dry precursor (10) with the balance of the lithium recirculated either as lithium hydroxide or lithium acetate excepting for typical manufacturing losses.

The acetic acid (17) can be a by-product of the reaction and not otherwise used or it may be a feedstock for preparation of the metal acetate (6).

As would be realized, the reaction scheme utilizing lithium hydroxide for pH adjustment allows for a closed loop wherein, at steady state, lithium and metals are added to the loop in a stoichiometric ratio, and removed in the same stoichiometric ratio with all other components, and particularly a portion of the water, remaining in the closed loop. With the inventive process the combined stoichiometric reaction is represented by Scheme 4:

$$2LiOH + CO_2 + MAc_2 \rightarrow MCO_3 + 2LiAc + H_2O \quad \text{Scheme 4}$$

wherein $MCO_3$ and one LiAc represents the desired precursor while one LiAc and one mole of water are the reaction products. When splitting of the salts is considered by the salt splitter ($S_3$) the sole products are water and a mole of acetic acid which may be utilized to form the metal acetate thereby further decreasing the number of virgin raw materials required. If the lithium acetate is split into lithium hydroxide and acetic acid the theoretical limit of the reaction to form a precursor to an NMC of nominal formula $LiMO_2$ is represented by Scheme 5:

$$LiOH + CO_2 + MAc_2 \rightarrow MCO_3 + LiAc + HAc \quad \text{Scheme 5,}$$

wherein, excluding water; lithium hydroxide, $CO_2$ and metal acetate are the sole materials added to the process and metal carbonate, lithium acetate and acetic acid are the sole materials removed from the process.

The inventive process is suitable for use with any metal which can be introduced as a soluble salt, preferably an acetate salt, and precipitated as a carboxylate. Particularly preferred metals are those metals suitable for the formation of an NMC cathode comprising nickel, manganese, cobalt and materials suitable as optionally dopants added thereto.

It is preferred that the ratios of metal introduced as acetates, and lithium introduced, preferably as hydroxides or carbonates, be in a ratio sufficient to achieve the chemical formula, after calcining, represented by:

$$Li_{2-x-y-z}Ni_xMn_yCo_zO_2$$

wherein $x+y+z \leq 1$.

More preferably, none of x, y or z are zero. In one embodiment at least one of x, y or z is 0.2-0.5 and in a particularly preferred embodiment x, y and z are each between 0.23 and 0.43; more preferably between 0.3 and 0.36 and most preferably x, y and z are approximately equal. In another embodiment x is greater than at least one of y or x. In a particularly preferred embodiment $x \geq y+z$.

If other salts are to be prepared the separation at $S_1$ can be adjusted to alter the stoichiometric ratio of lithium and metal. For the formation of spinels, for example, with a nominal chemical formula after calcining, represented by:

$$LiNi_xMn_yCo_zO_4$$

wherein $x+y+z \leq 2$ the solid containing component (9) would have a metal to lithium ratio of nominally 2:1 thereby increasing the relative amount of excess lithium in the liquid component (13). More preferably, $0.2 \leq x \leq 0.5$ and most preferably z is 0 for the spinels.

Dopants can be added to enhance the properties of the oxide such as electronic conductivity and stability. The dopant is preferably a substitutional dopant added in concert with the primary nickel, manganese and optional cobalt. The dopant preferably represents no more than 5 mole % of the oxide. Preferred dopants include Al, Gd, Ti, Zr, Mg, Ca, Sr, Ba, Mg, Cr, Cu, Fe, Zn, V and B with Al and Gd being particularly preferred.

When dopants are employed the metal introduced as acetates, and lithium introduced, preferably as hydroxide or carbonate, are preferably in a ratio sufficient to achieve the chemical formula, after calcining, represented by:

$$Li_{2-x-y-z}Ni_xMn_yCo_zE_aO_2$$

wherein $x+y+z+a \leq 1$ wherein $a \leq 0.05$.

More preferably, none of x, y or z are zero. In a particularly preferred embodiment at least one of x, y or z is 0.2-0.5 and in a particularly preferred embodiment x, y and z are each between 0.23 and 0.43; more preferably between 0.3 and 0.36 and most preferably x, y and z are approximately equal.

In another embodiment, when dopants are employed the metal introduced as acetates, and lithium introduced, preferably as hydroxide or carbonate, are preferably in a ratio sufficient to achieve the chemical formula, after calcining, represented by:

$$LiNi_xMn_yCo_zE_aO_4$$

wherein $x+y+z+a \leq 2$ wherein $a \leq 0.05$.

The mixer and reactors are represented herein as separate components for the purposes of illustration and clarity with the understanding that any two or more of the mixers and reactors can be a single unit. In a preferred embodiment the lithium hydroxide and optional recycled lithium acetate are combined in a first vessel ($M_1$), reacted with carbon dioxide to form lithium hydrogen-carbonate in a second vessel ($R_1$) followed by reacting with metal acetate in a third vessel ($R_2$). Lithium hydrogen carbonate is taken to mean any reaction product of lithium carbonate and carbon dioxide which significantly increases the solubility of the mixture beyond that of lithium carbonate at a given temperature and pressure. In a more preferred embodiment at least the first vessel and second vessel are the same vessel with the lithium hydroxide and optional recycled lithium acetate remaining therein for formation of the lithium bicarbonate. In a particularly preferred embodiment the lithium bicarbonate remains in the vessel of formation and is further reacted with metal acetate therein.

Splitter ($S_1$) separates a solid containing component (9) from a liquid containing component (13) wherein the solid containing component comprises lithium acetate and metal carbonate preferably in an intended stoichiometric ratio with some volume of water which will be ultimately removed from the process. While illustrated as a single operation ($S_1$), multiple operations may be combined for achieving the solid containing component with lithium acetate and metal carbonate in the desired molar ratio. In one embodiment splitter (S1) separates the metal carbonates as a cake with most of the lithium acetate passing through in a liquor such as in a filter process. An appropriate amount of liquor, and associated water, is then recombined with the cake to achieve the desired molar ratio of lithium acetate to metal carbonate. In another embodiment, the liquid containing soluble lithium acetate and water may be decanted, or otherwise removed, until a sufficient amount of solution remains to represent the desired molar ratio of lithium acetate to metal carbonate. Other techniques are known in the art for removing a desired amount of liquid from a liquid-solid two phase system, any of which could be utilized for achieving the desired solids containing component (9) having the desired molar ratio of soluble lithium acetate with precipitated metal carbonate. Separators for separating the solids containing component and the liquid component suitable for demonstration of the invention include centrifuges, decanters, and filters.

The drier ($D_i$) is not particularly limited herein with vented dryers, wherein the water is released to the atmosphere, or closed dryers, wherein the water is captured for subsequent use, being suitable for demonstration of the invention. Dryers suitable for demonstration of the invention include spray dryers, evaporative dryers, freeze dryers, fluid bed dryers, and rotary kiln driers.

The splitter ($S_2$) is not particularly limited herein as the purpose is to proportion a single flow into two or more flows of predetermined amount without substantive change thereto. Proportional valves can be used in a continuous mode wherein a fraction of the flow is redirected. Alternatively, valves may be operated on a time basis wherein flow is not redirected for a period of time and them all flow, or a majority of flow, is redirected during a different period of time. Combinations thereof may be employed.

The salt splitter ($R_3$) is not particularly limited herein as there are commercial separators capable of separating a solution which contains substantially lithium acetate into a solution which contains substantially lithium hydroxide and a second which contains substantially acetic acid. Particularly suitable salt splitters include ion exchange beds, electrochemical methods and the like. Particularly suitable techniques for separating the lithium acetate into lithium hydroxide and acetic acid include conventional electrodialysis cells, electrodialysis cells employing bipolar membranes and electrochemical salt splitting cells which produce oxygen and hydrogen on each anode and cathode respectively.

The furnace ($F_1$) is not particularly limited with any conventional furnace typically used for calcining precursors of metal oxides suitable for demonstration of the invention. The calcining temperature is preferably about 700-900° C. and the heating profile is not limited herein. Particularly suitable furnaces include box furnaces, rotary kiln tube furnaces, roller hearth furnace and fluid bed furnace.

Throughout the description the term "virgin" with reference to a reagent refers to reagents which are newly added to the process which are thereby distinguished from reagents which remain in the lithium recycle loop for the purposes of discussion.

The invention has been described with reference to the preferred embodiments without limit thereto. One of skill in the art would realize additional improvements and alterations which are not specifically set forth but are within the meets and bounds of the invention as more specifically set forth in the claims appended hereto.

The invention claimed is:

1. A process for forming a precursor to a lithium metal oxide comprising:
   providing lithium bicarbonate in a first aqueous mixture;
   reacting said lithium bicarbonate with metal acetate thereby forming a second aqueous mixture comprising metal carbonate, lithium acetate, acetic acid and water;
   neutralizing said acetic acid in said second aqueous mixture with lithium hydroxide thereby forming a third mixture comprising metal carbonate and lithium acetate;
   separating said third mixture into a fourth mixture and a fifth mixture wherein said fourth mixture comprises said metal carbonate and a first portion of said lithium acetate with said metal carbonate and said lithium acetate being in a predetermined molar ratio, and said fifth mixture comprises a second portion of said lithium acetate; and
   drying said fourth mixture thereby forming said precursor comprising metal carbonate and lithium acetate in said predetermined molar ratio.

2. The process for forming a precursor to a lithium metal oxide of claim 1 further comprising incorporating lithium acetate in said first aqueous solution.

3. The process for forming a precursor to a lithium metal oxide of claim 2 further comprising incorporating a stoichiometric excess of lithium acetate in said first aqueous mixture.

4. The process for forming a precursor to a lithium metal oxide of claim 2 wherein said lithium acetate is recycled lithium acetate.

5. The process for forming a precursor to a lithium metal oxide of claim 4 wherein said recycled lithium acetate is from said second portion of said fifth mixture.

6. The process for forming a precursor to a lithium metal oxide of claim 1 wherein said providing said lithium bicarbonate comprises reacting a lithium salt with carbon dioxide.

7. The process for forming a precursor to a lithium metal oxide of claim 6 wherein said lithium salt is selected from lithium carbonate and lithium hydroxide.

8. The process for forming a precursor to a lithium metal oxide of claim 7 wherein lithium hydroxide is virgin lithium hydroxide.

9. The process for forming a precursor to a lithium metal oxide of claim 7 wherein lithium hydroxide is recycled lithium hydroxide.

10. The process for forming a precursor to a lithium metal oxide of claim 9 further comprising converting at least a fraction of said second portion of said lithium acetate into said recycled lithium hydroxide.

11. The process for forming a precursor to a lithium metal oxide of claim 1 wherein said separating said third mixture into said fourth mixture and said fifth mixture comprises forming a solids containing component comprising said metal carbonate.

12. The process for forming a precursor to a lithium metal oxide of claim 11 further comprising forming a metal carbonate depleted lithium acetate solution.

13. The process for forming a precursor to a lithium metal oxide of claim 12 further comprising adding a portion of said metal carbonate depleted lithium acetate solution to said solids containing component.

14. The process for forming a precursor to a lithium metal oxide of claim 11 further comprising adding a lithium acetate solution to said solids containing component.

15. The process for forming a precursor to a lithium metal oxide of claim 1 wherein said metal acetate comprises at least one metal selected from the group consisting of nickel, manganese and cobalt.

16. The process for forming a precursor to a lithium metal oxide of claim 15 wherein said metal acetate comprises at least one metal selected from the group consisting of nickel, manganese and cobalt.

17. The process for forming a precursor to a lithium metal oxide of claim 1 wherein said predetermined molar ratio is about 1:1.

18. The process for forming a precursor to a lithium metal oxide of claim 1 wherein said separating comprises a separator selected from a filter, a decanter and a centrifuge.

19. The process for forming a precursor to a lithium metal oxide of claim 1 wherein said drier is selected from a spray drier, an evaporative dryer, a freeze dryer, a fluid bed drier and a rotary kiln drier.

20. A process for forming a metal oxide comprising calcining said precursor to a lithium metal oxide of claim 1 to form an oxide.

21. The process for forming a lithium metal oxide of claim 20 wherein said calcining is at a temperature of from 700-900° C.

22. The process for forming a lithium metal oxide of claim 20 wherein said metal oxide has a formula represented by:

$$Li_{2-x-y-z}Ni_xMn_yCo_zO_2$$

wherein $x+y+z \leq 1$.

23. The process for forming a lithium metal oxide of claim 22 wherein none of x, y or z are zero.

24. The process for forming a lithium metal oxide of claim 22 wherein at least one of x, y or z is 0.2-0.5.

25. The process for forming a lithium metal oxide of claim 22 wherein x, y and z are each between 0.23 and 0.43.

26. The process for forming a lithium metal oxide of claim 25 wherein x, y and z are each between 0.3 and 0.36.

27. The process for forming a lithium metal oxide of claim 26 wherein x, y and z are approximately equal.

28. The process for forming a lithium metal oxide of claim 20 wherein said lithium metal oxide has a formula represented by:

$$Li_{2-x-y-z}Ni_xMn_yCo_zE_aO_2$$

wherein $x+y+z+a \leq 1$; and

E is a dopant.

29. The process for forming a lithium metal oxide of claim 28 wherein none of x, y or z are zero.

30. The process for forming a lithium metal oxide of claim 28 wherein at least one of x, y or z is 0.2-0.5.

31. The process for forming a lithium metal oxide of claim 28 wherein x, y and z are each between 0.23 and 0.43.

32. The process for forming a lithium metal oxide of claim 31 wherein x, y and z are each between 0.3 and 0.36.

33. The process for forming a lithium metal oxide of claim 32 wherein x, y and z are approximately equal.

34. The process for forming a lithium metal oxide of claim 28 wherein a is no more than 0.05.

35. The process for forming a lithium metal oxide of claim 28 wherein said dopant is selected from the group consisting of Al, Gd, Ti, Zr, Mg, Ca, Sr, Ba, Mg, Cr, Cu, Fe, Zn, V and B.

36. The process for forming a lithium metal oxide of claim 35 wherein said dopant is selected from the group consisting of Al and Gd.

37. The process for forming a lithium metal oxide of claim 20 wherein said calcining is at a temperature of from 700-900° C.

38. The process for forming a lithium metal oxide of claim 20 wherein said metal oxide has a formula represented by:

$$LiNi_xMn_yCo_zO_4$$

wherein $x+y+z \leq 2$.

39. The process for forming a lithium metal oxide of claim 38 wherein none of x, y or z are zero.

40. The process for forming a lithium metal oxide of claim 38 wherein at least one of x is 0.2-0.5.

41. The process for forming a lithium metal oxide of claim 40 wherein z is 0.

42. The process for forming a lithium metal oxide of claim 20 wherein said lithium metal oxide has a formula represented by:

$$LiNi_xMn_yCo_zE_aO_4$$

wherein $x+y+z+a \leq 2$; and

E is a dopant.

43. The process for forming a lithium metal oxide of claim 42 wherein none of x, y or z are zero.

44. The process for forming a lithium metal oxide of claim 42 wherein at least one of x, y or z is 0.2-0.5.

45. The process for forming a lithium metal oxide of claim 42 wherein z is 0.

46. The process for forming a lithium metal oxide of claim 42 wherein a is no more than 0.05.

47. The process for forming a lithium metal oxide of claim 42 wherein said dopant is selected from the group consisting of Al, Gd, Ti, Zr, Mg, Ca, Sr, Ba, Mg, Cr, Cu, Fe, Zn, V and B.

48. The process for forming a lithium metal oxide of claim 47 wherein said dopant is selected from the group consisting of Al and Gd.

49. A process for forming a precursor to a lithium metal oxide comprising:
providing lithium bicarbonate in a first aqueous mixture;
reacting said lithium bicarbonate with metal complexed with the base of an organic acid thereby forming a second aqueous mixture comprising metal carbonate, lithium organic acid salt, said organic acid and water;

neutralizing said organic acid in said second aqueous mixture with lithium hydroxide thereby forming a third mixture comprising metal carbonate and lithium salt of said organic acid;

separating said third mixture into a fourth mixture and a fifth mixture wherein said fourth mixture comprises said metal carbonate and a first portion of said lithium salt of said organic acid with said metal carbonate and said lithium salt of said organic acid being in a predetermined molar ratio, and said fifth mixture comprises a second portion of said lithium salt of said organic acid; and drying said fourth mixture thereby forming said precursor comprising metal carbonate and lithium salt of said organic acid in said predetermined molar ratio.

50. The process for forming a lithium metal oxide of claim 49 wherein said organic acid comprises at least one carboxylic acid group.

51. The process for forming a lithium metal oxide of claim 50 wherein said organic acid comprises no more than three carboxylic acid groups.

52. The process for forming a lithium metal oxide of claim 50 wherein said organic acid comprises two carboxylic acid groups.

53. The process for forming a lithium metal oxide of claim 49 wherein said organic acid comprises no more than 10 alkyl carbons.

54. The process for forming a lithium metal oxide of claim 53 wherein said organic acid comprises no more than 5 alkyl carbons.

55. The process for forming a lithium metal oxide of claim 49 wherein said organic acid is selected from acetic acid and oxalic acid.

* * * * *